United States Patent [19]

Serafini et al.

[11] Patent Number: 5,432,001
[45] Date of Patent: Jul. 11, 1995

[54] CONCENTRATED PREPOLYMER COMPOSITION USEFUL FOR FORMING POLYIMIDE ARTICLES

[75] Inventors: Tito T. Serafini, Redlands; Paul G. Cheng, Rancho Palos Verdes; Ward F. Wright, Redondo Beach, all of Calif.

[73] Assignee: TRW Inc., Redondo Beach, Calif.

[21] Appl. No.: 265,581

[22] Filed: Jun. 23, 1994

Related U.S. Application Data

[63] Continuation-in-part of Ser. No. 816,304, Dec. 27, 1991, Pat. No. 5,338,827, which is a continuation-in-part of Ser. No. 472,036, Jan. 30, 1990, Pat. No. 5,091,505, and a continuation-in-part of Ser. No. 472,198, Jan. 30, 1990, Pat. No. 5,132,395.

[51] Int. Cl.⁶ .................................................. D02G 3/40
[52] U.S. Cl. ............................ 428/395; 428/364; 428/370; 428/375; 428/473.5; 528/271; 528/351; 528/353; 528/481; 528/503; 524/765; 524/772
[58] Field of Search ............... 428/364, 370, 375, 395, 428/473.5; 528/271, 351, 353, 481, 503; 524/765, 772

[56] References Cited

U.S. PATENT DOCUMENTS

| | | | |
|---|---|---|---|
| 3,179,631 | 4/1965 | Endrey | 528/353 |
| 3,179,633 | 4/1965 | Endrey | 528/353 |
| 3,249,588 | 5/1966 | Gall | 528/353 |
| 3,407,176 | 10/1968 | Loncrini | 528/185 |
| 3,459,706 | 8/1969 | Schweitzer | 528/128 |
| 3,505,295 | 4/1970 | Grundsteidl et al. | 528/322 |
| 3,745,149 | 7/1973 | Serafini et al. | 528/288 |
| 3,775,434 | 11/1973 | Spietschka | 549/232 |
| 3,998,786 | 12/1976 | D'Alelio | 528/353 |
| 4,058,505 | 11/1977 | D'Alelio | 528/353 |
| 4,061,856 | 12/1977 | Hsu | 528/353 |
| 4,094,862 | 6/1978 | Bell | 528/353 |
| 4,111,906 | 9/1978 | Jones et al. | 528/229 |
| 4,159,262 | 6/1979 | Hsu | 528/342 |
| 4,166,170 | 8/1979 | St. Clair | 528/229 |
| 4,173,700 | 11/1979 | Green et al. | 528/352 |

(List continued on next page.)

FOREIGN PATENT DOCUMENTS

| | | |
|---|---|---|
| 0395020A2 | 10/1990 | European Pat. Off. |
| 0420593A2 | 4/1991 | European Pat. Off. |
| 0439915A1 | 8/1991 | European Pat. Off. |
| 0439916A1 | 8/1991 | European Pat. Off. |
| 57-26131 | 6/1982 | Japan |
| 63-172736 | 7/1988 | Japan |
| 63-248828 | 10/1988 | Japan |
| 1135765 | 5/1989 | Japan |
| 1139632 | 6/1989 | Japan |
| 3-9930 | 1/1991 | Japan |
| 4-213325 | 8/1992 | Japan |

OTHER PUBLICATIONS

Letter to P. G. Cheng from Air Force, dated Jun. 25, 1990.

News Release, Dexter Corporation, *AFR-700 Resins*, Feb. 15, 1991, and customer list/amount sold as of Jun. 25, 1990, Cleveland, Ohio.

(List continued on next page.)

*Primary Examiner*—Samuel A. Acquah
*Attorney, Agent, or Firm*—Sheldon & Mak; Sol L. Goldstein

[57] ABSTRACT

A method for forming a homogeneous, concentrated, prepolymer composition, and a method of using the concentrated prepolymer composition to uniformly coat fibers is described. The prepolymer mixture is formed by dissolving a dialkyl, trialkyl, or tetraalkylester of biphenyltetracarboxylic acid in a solvent comprising ethyl acetate and methanol in a molar ratio of from about 1:3 to about 1:60, to form an ester solution. Diamine and end cap compound are added to the ester solution to form a monomer mixture solution. The end cap compound is a divalent compound characterized by (i) at least one unsaturated moiety, (ii) capable of reacting with the diamine or the ester to form an end cap radical that precludes further reaction of the diamine with the ester, and (iii) capable of undergoing addition polymerization. A portion of the solvent is evaporated from the monomer solution to form the substantially homogeneous, concentrated, prepolymer composition. The concentrated prepolymer composition is used to uniformly coat fibers by heating the composition to an elevated temperature to form a prepolymer melt and applying the prepolymer melt to fibers. An article of manufacture comprising fibers and polyimide can be formed by heating the prepolymer coated fibers to the cross-linking temperature of the prepolymers.

5 Claims, No Drawings

U.S. PATENT DOCUMENTS

| | | | |
|---|---|---|---|
| 4,183,839 | 1/1980 | Gagliani | 524/719 |
| 4,189,560 | 2/1980 | Roth et al. | 526/259 |
| 4,203,922 | 5/1980 | Jones et al. | 564/315 |
| 4,209,598 | 6/1980 | Patzschke | 525/333 |
| 4,238,538 | 12/1980 | Manwiller | 428/35.7 |
| 4,302,413 | 11/1981 | Howe et al. | 264/126 |
| 4,391,967 | 7/1983 | Nimry et al. | 528/189 |
| 4,417,045 | 11/1983 | Nimry et al. | 528/188 |
| 4,440,643 | 4/1984 | Makino et al. | 210/500.2 |
| 4,456,653 | 6/1984 | Rüegg et al. | 428/379 |
| 4,497,948 | 2/1985 | Lauver | 528/342 |
| 4,499,042 | 2/1985 | Ishizuka et al. | 264/205 |
| 4,552,931 | 11/1985 | St. Clair et al. | 525/432 |
| 4,629,777 | 12/1986 | Pfeifer | 528/353 |
| 4,755,555 | 7/1988 | Manwiller et al. | 524/607 |
| 4,778,872 | 10/1988 | Sasaki et al. | 528/176 |
| 4,801,682 | 1/1989 | Scola | 528/353 |
| 4,914,182 | 4/1990 | Pfeifer et al. | 528/353 |
| 4,956,450 | 9/1990 | Lee et al. | 528/353 |
| 4,963,645 | 10/1990 | Inoue et al. | 528/342 |
| 4,973,661 | 11/1990 | Lee et al. | 528/353 |
| 4,973,662 | 11/1990 | Odagiri et al. | 528/353 |
| 5,091,505 | 2/1992 | Serafini et al. | 528/353 |
| 5,132,395 | 7/1992 | Serafini et al. | 528/353 |
| 5,145,916 | 9/1992 | Yamamoto et al. | 525/421 |
| 5,149,760 | 9/1992 | Serafini et al. | 528/353 |
| 5,149,772 | 9/1992 | Serafini et al. | 528/353 |
| 5,162,492 | 11/1992 | Kaku | 528/353 |
| 5,173,561 | 12/1992 | Gupta | 528/183 |

OTHER PUBLICATIONS

News Release, TRW, *TRW Develops. Markets New High Temperature Polymer Family*, Nov. 7, 1991; TRW Redondo Beach, Calif.

*Matrix Resin Development, Volume II, Technical Proposal*, Feb. 29, 1988, prepared for Northrop Corporation.

PCT Search Report mailed Nov. 2, 1992, for PCT/US92/03285.

Proceedings of the AFR–700 Symposium, dated Sep. 24, 1991.

*Structural Composite Materials (STRCM)*, AFWAL/AFML/DARPA Contract No. F33615-88-C-5409, Interim Report for period of Feb. 1989–Jul. 1989.

Submission to the General Electric Company for study entitled, *Processable 700°F Matrix Resins*, Sep. 28, 1987.

Technical Progress Reports entitled, *Matrix Resin Development* from TRW to Northrup Corporation.

Billmeyer, Jr., Fred W., *Textbook of Polymer Science*, 2d Ed., John Wiley and Sons, Inc., New York, p. 231.

Brown, Alan, The Air Force Finds an Ultrahigh-temperature Resin, *Materials Notebook*, Aerospace America, Oct. 1991.

Browning, Charles E., New Applications from New Materials, *Advanced Thermoset Composites*, Van Nostrad Reinhold, New York, pp. 1–20.

Delvigs, Peter, et al., *Addition Type Polyimides from Solutions of Monomeric Reactants*, NASA TN D–6877, Aug. 1972.

Delvigs, Peter, *371°C Mechanical Properties of Graphite/Polyimide Composites*, NASA, pp. 314–323.

Hergenrother, P. M., Condensation Polyimides, in *Encyclopedia of Composites*, S. M. Lee, Ed. BCH Publisher, Inc., New York. vol. 4, 1991. pp. 180–196.

Hurwitz, Frances I., *Influence of Excess Diamine on Properties of PMR Polyimide Resins and Composites*, NASA TM X–81580, 1980.

Meares, Patrick, *Polymers Structure and Bulk Properties*, D. Van Nostrand Company, Ltd., London, p. 265.

Morrison, Robert T., et al., *Organic Chemistry*, 3d Ed., Allyn and Bacon, Inc., Boston, p. 730.

Serafini, Tito T., PMR Polyimide Composites for Aerospace Applications, in *Polyimides*, edited by K. L. Mittal, Plenum Press, New York, pp. 957–975.

Serafini, Tito T., et al., Thermally Stable Polyimides from Solutions of Monomeric Reactants, *Journal of Applied Polymer Science*, 16:905–1915 (1972).

Serafini, Tito, T., et al., *Tailor Making High Performance Graphite Fiber Reinforced PMR Polyimides*, NASA TM X–71616, Society of the Plastics Industry, Washington, D.C., 1975.

Serafini, Tito T., et al., *Second Generation PMR Polyimides*, NASA TM X–71894, Society for the Advancement of Material and Process Engineering, Los Angeles, Calif., 1976.

Serafini, Tito, T., *Processable High Temperature Resistant Polymer Matrix Materials*, Proceedings ICCM I, vol. 1, AIME, New York, 1976.

Serafini, Tito T., High–temperature Resins, Chapter 6 in *Handbook of Composites*, G. Lubin, Ed., Van Nostrand Reinhold, 1982, pp. 89–113.

St. Clair, Terry L., et al., *Solventless LARC–160 Polyimide Matrix Resins*, NASA TM–74944, Anaheim, Calif., 1978.

Vannucci, Raymond D., *PMR Polyimide Compositions for Improved Performance at 371°C*, 32nd International SAMPE Symposium, Apr. 6–9, 1987.

Vannucci, Raymond D., PMR Polyimide Compositions for Improved Performance at 371°C, *SAMPE Quarterly*, Oct. 1987, pp. 31–36.

CONCENTRATED PREPOLYMER COMPOSITION USEFUL FOR FORMING POLYIMIDE ARTICLES

CROSS-REFERENCE

This application is a continuation-in-part of U.S. Pat. No. 5,338,827, U.S. patent application Ser. No. 07/816,304, filed on Dec. 27, 1991, by Serafini, et al., and entitled "POLYIMIDE RESINS USEFUL AT HIGH TEMPERATURES," which is a continuation-in-part of Ser. No. 07/472,036 filed Jan. 30, 1990 now U.S. Pat. No. 5,091,505 and Ser. No. 07/472,198 filed Jan. 30, 1990 now U.S. Pat. No. 5,132,395. This application is also related to U.S. Pat. Nos. 5,149,760 and 5,149,772. All of these applications and patents are incorporated herein by reference.

BACKGROUND

This invention relates to a homogenous, concentrated, prepolymer composition useful for forming polyimide articles, such as polyimide composites.

Polyimide resins are used to form structural components for military and civil aviation applications, such as jet engine cowls and ducts. Polyimides useful for these applications are lightweight, have superior load-bearing characteristics, and have glass transition temperatures ($T_g$) substantially above the temperature at which the composite is used to preclude softening and creep. Also, the polyimide must have good thermo-oxidative stability at high temperatures (typically from 500° F. to 700° F.). High thermo-oxidative stability is indicated by low weight loss after long term, high temperature, exposure to oxidative environments. For example, our U.S. Pat. Nos. 5,091,505 and 5,132,395 teach polyimides which are thermally stable at temperatures of up to 700° F., and our co-pending U.S. patent application Ser. No. 07/816,304, filed on Dec. 27, 1991, describes a specific formulation of monomeric reactants which form polyimides thermally stable at temperatures of up to 800° F. The monomeric reactants taught by the latter application comprise: (a) an ester of biphenyltetracarboxylic acid, (b) phenylenediamine, and (c) a divalent end cap compound capable of reacting with the phenylenediamine or the ester to form an end cap radical that precludes further reaction of the phenylenediamine with the ester.

Generally, the fiber reinforced polyimide structural components comprise fibers such as glass, ceramic, or carbon fibers, embedded in a polyimide matrix. Typically, the structural component is made by the steps of (i) forming a low concentration monomeric reactant solution, (ii) impregnating fibers with the low concentration solution to coat the fibers with the monomeric reactants, (iii) forming the coated fibers into a structural component, and (iv) polymerizing the monomeric reactants on the fibers in situ to form a fiber reinforced polyimide composite. For example, our aforementioned co-pending application Ser. No. 07/816,304, discloses a low concentration monomeric reactant solution that comprises 37% monomer by weight in methanol. Conventional solvent, such as methanol, is capable of dissolving only up to about 30% to 40% by weight of monomer. Attempting to dissolve additional monomer can cause the dissolved monomers to precipitate from the solution.

There are several problems with the use of low concentration solutions for impregnating reinforcing fibers. One problem is that the low concentration (or low solids content) of these solutions necessitates multiple fiber impregnation steps to obtain a sufficiently thick coating of the monomers onto the fibers. The multiple impregnation steps are inefficient and costly. Also, the multiple impregnation steps can result in a non-uniform coating of monomeric reactants on the fibers. The non-uniform coating results in a composite having non-uniform loading bearing properties caused by variations in distribution of fibers within the composite. Variations in fiber content can also cause separation and delamination between fiber layers.

Another problem with the low concentration monomeric reactant solutions is that a large percentage (about 50% by volume) of solvent is needed to completely dissolve the monomeric reactants. The solvent volatilizes during the curing of the composite, forming large amounts of gaseous byproducts which form voids within the molded composite. These voids further weaken the load bearing capability of the composite, and also reduce the thermo-oxidative stability of the composite.

A further problem with the use of the low concentration monomeric solutions is their relatively short shelf life. The short shelf life occurs because the monomers dissolved in the solvent precipitate out of the solution when the solution is stored for a period of time. For example, our application Ser. No. 07/816,304, discloses a methanolic reactant solution which has a shelf life of about 24 hours to about 48 hours, because when stored for a longer period of time, the ester of biphenyltetracarboxylic acid in the solution precipitates out from the solution. A short shelf life is commercially undesirable because it necessitates preparation of the monomeric reactant solutions immediately prior to their use.

Thus, there is a need for a method of preparing a substantially homogenous, concentrated, prepolymer composition suitable for uniformly coating fibers. It is also desirable for the prepolymer composition to contain reduced amounts of solvent to reduce outgassing during curing of the prepolymer and to increase the uniformity of the coating on the fibers. It is also desirable for the prepolymer composition to have an extended shelf life, be affordable and non-toxic, and be capable of use to fabricate composites using conventional molding equipment.

SUMMARY

The present invention provides a substantially homogenous, concentrated, prepolymer composition that is capable of uniformly coating fibers that satisfies these needs.

The substantially homogeneous, concentrated, prepolymer composition is formed by the following steps. A concentrated ester solution is formed by dissolving a dialkyl, trialkyl, or tetraalkylester of biphenyltetracarboxylic acid in a solvent comprising ethyl acetate and methanol, the molar ratio of ethyl acetate to methanol being from about 1:3 to about 1:60. The concentration of ester in the ester solution is preferably at least about 50% by weight, and more preferably at least about 70% by weight.

Diamine and end cap compound are added to the ester solution to form a monomer solution. The end cap compound is capable of reacting with the diamine or the ester to form an end cap radical that precludes further reaction of the diamine with the ester. Typically, the end cap compound is divalent, has at least one unsaturated moiety, and is capable of undergoing addition polymerization.

A substantially homogeneous, concentrated, prepolymer composition is formed by evaporating a portion of the solvent from the monomer solution. The concentrated prepolymer composition is used to uniformly coat the fibers by heating the composition to a temperature sufficiently high to melt the prepolymer composition, but below the curing temperature of the prepolymers, to uniformly impregnate and coat the fibers. After the fibers are uniformly coated, a composite article is formed using the coated fibers. Thereafter, the composite article is heated to a temperature sufficiently high to cross-link and cure the prepolymers around the fibers, to form a fiber-reinforced polyimide composite.

The fiber-reinforced polyimide composites prepared in accordance with the present invention are capable of use at elevated temperatures, have substantially uniform loading bearing properties, and can be prepared from low cost, non-toxic monomers.

These and other features, aspects, and advantages of the present invention will become better understood with reference to the following description and appended claims.

DESCRIPTION

According to this invention, high temperature polyimide composites are fabricated using a substantially homogeneous, concentrated, prepolymer composition that can be used to uniformly coat fibers for fabricating fiber-reinforced composite articles.

Generally, the method comprises the steps of (i) forming an ester solution comprising a dialkyl, trialkyl, or tetraalkylester of biphenyltetracarboxylic acid in a solvent, the solvent comprising ethyl acetate and methanol in a molar ratio from about 1:3 to about 1:60, (ii) adding diamine and end cap compound to the ester solution to form a monomer solution, the end cap compound capable of reacting with the diamine or the ester to form an end cap radical that precludes further reaction of the diamine with the ester, and (iii) evaporating a portion of the solvent from the monomer solution to form a substantially homogeneous, concentrated, prepolymer composition that is capable of cross-linking to form thermally stable polyimides, the concentration of the prepolymer in the prepolymer composition being as much as about 50–60% by weight. Each of these steps and the compounds used therein are described in more detail below.

Ester Solution

The ester solution comprises a dialkyl, trialkyl, or tetraalkylester of biphenyltetracarboxylic acid dissolved in a solvent comprising ethyl acetate and methanol. The ester of biphenyltetracarboxylic acid can be readily prepared from the corresponding dianhydrides of the formula:

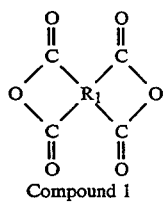

Compound 1 in which $R_1$ is a divalent biphenyl moiety. For example, the ester can be conveniently prepared from the 3,3',4,4' biphenyltetracarboxylic dianhydride, or its isomers, such as 2,3,3',4' or 2,2',3,3' biphenyltetracarboxylic dianhydride.

Diamine

Diamines useful in the present invention comprise para-phenylenediamine, meta-phenylenediamine, 4,4'-methylenedianiline, 4,4'-diaminodiphenylsulphone, and 4,4'-oxydianiline. Preferably, the diamine comprises phenylenediamines having the structural formula:

$$H_2N—R_2—NH_2 \qquad \text{Compound 2}$$

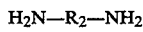

where, $R_2$ is a divalent phenyl moiety. Representative phenylenediamines useful in the present invention comprise meta-phenylenediamine and paraphenylenediamine.

As disclosed in our aforementioned pending application Ser. No. 07/816,304, excellent high temperature properties are obtained if the diamine comprises para-phenylenediamine and meta-phenylenediamine or only meta-phenylenediamine. When the diamine comprises a mixture of meta- and para-phenylenediamine, preferably the ratio of meta-phenylenediamine to para-phenylenediamine is at least about 1:1, and more preferably is from about 3:2 to about 4:1. The phenylenediamine is also advantageous because it is non-toxic and avoids the danger of toxicity associated with the use of amines such as 4,4'-methylenedianiline.

End Cap

The end cap compound controls the average molecular weight of the prepolymers formed in the polymerization of the ester and diamine, by reacting with either the ester or diamine. The end cap compound is divalent and is characterized by (i) having at least one unsaturated moiety, (ii) being capable of reacting with the phenylenediamine or the ester to form an end cap radical that precludes further reaction of the phenylenediamine with the ester, and (iii) being capable of undergoing addition polymerization.

When the end cap compound reacts with the diamine to produce $E_1$, the end cap compound can be:

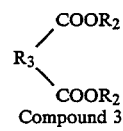

Compound 3 where at least one of $R_2$ is alkyl and $R_3$ is a divalent radical of either of the formulas:

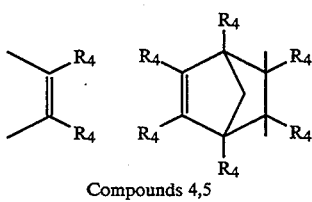

Compounds 4,5 where each $R_4$ is independently selected from the group consisting of hydrogen and lower alkyls, normally one to four carbon atoms.

The mono- or dialkyl ester of the dicarboxylic acid (compound 3) can be prepared from the corresponding anhydride. Representative of such dianhydrides include maleic anhydride, citraconic anhydride, 5-norbornene-2,3-dicarboxylic anhydride, and alkyl or alkenyl substituted 5-norbornene-2,3-dicarboxylic anhydride.

Suitable end cap compounds for reacting with the ester to produce $E_2$ are amino compounds with the structure $R_6NH_2$, where $R_6$ is a moiety capable of addition polymerization. These include p-ethynylaniline (p-aminophenyllacetylene), p-aminostyrene, and (4-aminobenzo)cyclobutene.

Preparation of Homogenous, Concentrated, Prepolymer Composition

An ester solution is prepared in situ from the dianhydride by dissolving the dialkyl, trialkyl, or tetraalkylester of biphenyl-tetracarboxylic acid in a solvent comprising a mixture of ethyl acetate and methanol, the molar ratio of ethyl acetate to methanol being from about 1:3 to about 1:60. It has been discovered that this solvent mixture allows dissolution of a high concentration of ester. The ester concentration in the ester solution can exceed 50% by weight, or even exceed 70% by weight, without precipitation of the ester. Preferably, the ethyl acetate to methanol molar ratio in the solvent is from about 1:3 to about 1:20, and more preferably is from about 1:4 to about 1:8, and most preferably is about 1:5.

To form the ester solution in the ethyl acetate and methanol, the corresponding dianhydride is added to the solution, and the solution is heated to reflux for about 15 to 24 hours, and more preferably for about 19 hours. The solution is then cooled to room temperature.

The selected diamine and end cap are each dissolved in organic solvents to form separate diamine and end cap solutions. Suitable solvents for dissolving the diamine and end cap include aliphatic alcohol, aliphatic ether, aprotic solvent, such as N,N-dimethylformamide and dimethylsulfoxide, and mixtures thereof. The selected solvent should be inert to the diamine and end cap, and should be compatible with the ester solution, which comprises ethyl acetate and methanol. Each of the solutions are separately prepared.

A monomer solution is prepared by adding diamine and end cap solutions to the ester solution. The monomer solution is stirred at room temperature (25° C.) for about 24 hours. At least a portion of the solvent in the monomer solution evaporates during this step, providing a homogenous, concentrated, prepolymer composition having a solidified waxy or paste-like consistency. The concentration of the prepolymer in the prepolymer composition is typically at least about 50% by weight. Preferably, the concentration of prepolymer is in the range of 80–90% with about 10–20% solvent by weight.

An important commercial advantage of the concentrated prepolymer composition is its extended shelf life. The prepolymer composition can have a shelf life at least one week, and more typically at least two weeks or three weeks. This allows ease of preparation and shipping of the prepolymer composition, which is commercially highly desirable.

The solidified prepolymer composition can be used to uniformly coat fibers by heating the prepolymer composition to a sufficiently high temperature to melt the prepolymer composition, generally from about 80° C. to about 120° C., and more preferably about 100° C. Suitable reinforcing fiber, such as glass, ceramic or polymer fibers, are dipped or impregnated with the prepolymer melt, to uniformly coat the fibers. Suitable fibers include "E" and "S" type glass fibers manufactured by Corning Glass Company, Corning, N.Y., and carbon fibers manufactured by Amoco Performance Products of Alpharetta, Ga. The concentrated, high viscosity, prepolymer melt allows coating the fibers with a 40–60% weight fraction of prepolymer in a single dipping step without necessitating multiple dipping steps. Also, the absence of solvent in the prepolymer composition promotes more uniform coating of the fibers and reduces outgassing and resultant pore formation and delamination, when the prepolymers on the fibers are cured.

In some applications, it is preferred to use the prepolymer composition without the use of any reinforcing fibers. For example, the prepolymer composition can also be used to form molded or cast polyimide articles having high temperature capability which do not use reinforcing fibers. Conventional molding and casting techniques can be used for forming such polyimide articles.

Imidization

The prepolymer coating on the fibers is imidized by heating the coated fibers to sufficiently high temperature to imidize the prepolymers, generally to a temperature of about 150° C. to about 308° C., and preferably about 200° C. for about 15 minutes to 1 hour, and more preferably about 30 minutes.

The structure, terminal moieties and molecular weights of the imidized prepolymers formed in the imidization step depend on the molar ratio of ester, phenylenediamine and end cap. Also, depending on the molar ratio of the reactants, the prepolymers have either a single or doubly end capped structure as described below.

When the end cap compound reacts with the diamine, and the molar ratio of the ester, diamine, and end cap compound is n:n+1:2, the prepolymer formed is believed to have the structure:

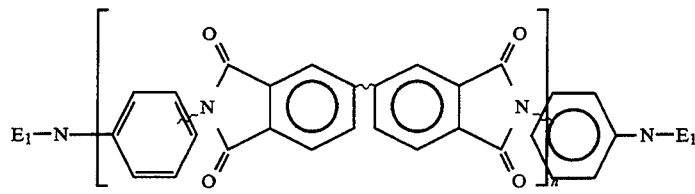

Compound 6

When the end cap compound reacts with the diamine, and the molar ratio of the ester, diamine, and end cap compound is n:n:1, the prepolymer formed is believed to have the structure:

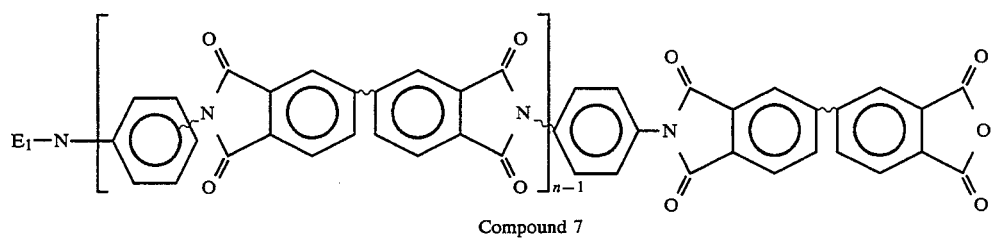

Compound 7

When the end cap compound reacts with the diamine, and the molar ratio of the ester, diamine, and end cap compound is n:n+1:1, the prepolymer formed is believed to have the structure:

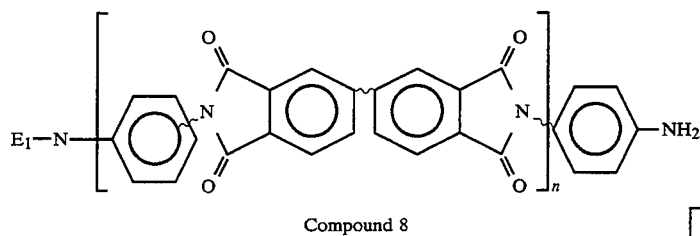

Compound 8

When the end cap compound reacts with the ester, and the molar ratio of the ester, diamine, and end cap compound is n+1:n:2, the prepolymer formed is believed to have the structure:

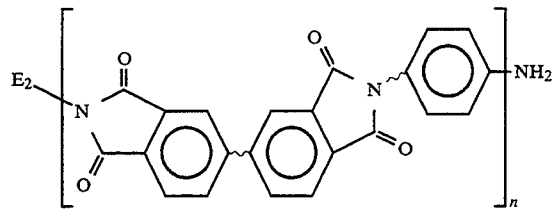

Compound 11

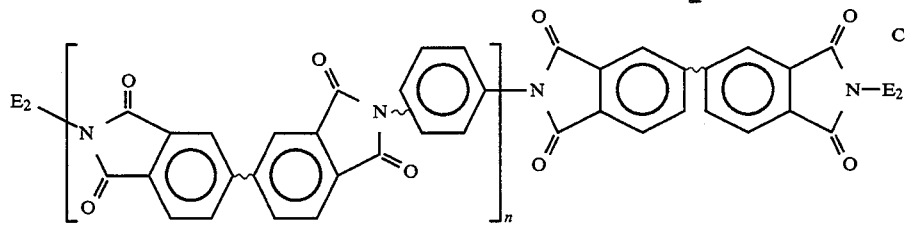

Compound 9

When the end cap compound reacts with the ester, and the molar ratios of the ester, diamine, and end cap compound are n+1:n:1, the prepolymer formed is believed to have the structure:

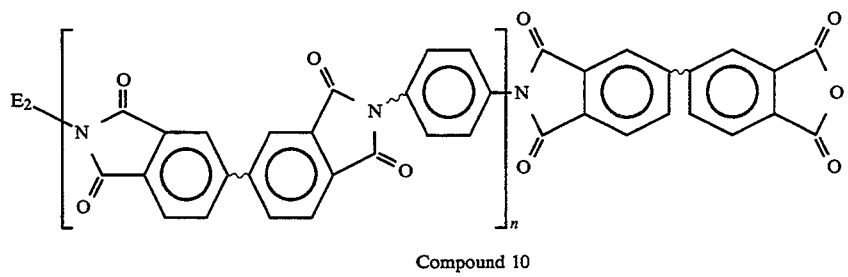

Compound 10

When the end cap compound reacts with the ester, and the molar ratios of the ester, diamine, and end cap compound are n:n:1, the prepolymer formed is believed to have the structure:

For compounds 7–11, the number "n" ranges between 2 and 20, and generally is sufficiently small that the molecular weight of the prepolymer is less than about 50,000, and preferably less than about 10,000. Also, $E_1$ and $E_2$ are the end cap radicals provided by the end cap compound. The end cap radical has at least one unsaturated moiety and is capable of undergoing addition polymerization.

The exact structure of any of compounds 6–11 is unknown, and the structures presented are those believed most likely to result from the type of monomers and stoichiometry used to prepare the compounds. For example, Compounds 7 and 10 are shown as being anhydrides, however, these compounds could just as likely be esters instead of anhydrides. Thus, although compounds 7 and 10 are shown in this description and the claims as being anhydrides, the formulas are intended to represent the ester equivalents of the anhydrides.

Curing

The fibers with the imidized prepolymer coating can be molded to form composite structures using conventional molding and curing techniques. After lay-up of the fibers into the desired composite structure, the structure is cured at elevated temperatures and pressures under 200 psi to cross-link the prepolymers, forming macromolecular polyimides with use temperatures as high as 800° F. Macromolecular polyimides are prepared when the imide prepolymers are heated at elevated temperature, generally at least about 600° F., and typically in the range of from about 600° to about 700° F. Heating is carried out for a sufficient time to cross-link the prepolymer forming thermally stable polyimide resins believed to have an average molecular weight in excess of 50,000. Because the polyimide resin formed is cross-linked, the exact molecular weight of the resin is not known.

Preferably the polyimide resin is postcured by heating in air after cross-linking. A preferred temperature cycle for postcuring comprises maintaining the resin at about 600° F. for about 16 hours, about 625° F. for about 2 hours, about 650° F. for about 4 hours, about 675° F. for about 2 hours, about 700° F. for about 4 hours, about 725° F. for about 2 hours, and about 750° F. for about 4 hours.

Applications

Polyimide resins of the present invention have many applications. For example, the polyimide resin can be used to form the matrix of fiber reinforced composite materials which are useful as light weight structural components in aircraft engines and air frames. Among the fiber reinforcement materials that can be used are carbon, ceramic, glass, silicon carbide, silicon nitride, and refractory metals such as tungsten.

Another application for the polyimide resins is use as an adhesive, particularly as adhesives for joining high temperature composite structures made of polyimide resins.

The polyimide resins can also be used for molding, such as by injection molding or resin transfer molding. They can also be used as a protective coating for providing protection against high temperatures and/or oxidizing conditions.

Advantages

The homogenous, concentrated prepolymer composition of the present invention has several important advantages. First, the prepolymer composition is homogenous, allowing uniform coating of fibers. Second, the prepolymer composition is concentrated, having a prepolymer concentration of as much as 80% to 90%. The high concentration of prepolymer allows coating of fibers in a single step impregnation operation, without necessitating multiple impregnation steps.

The substantial absence of solvent in the concentrated prepolymer composition reduces outgassing and resultant void formation when the composite lay-up is cured.

Also, the prepolymer has an extended shelf life which can exceed one to two weeks. The extended shelf life provides significant commercial advantages for shipping and distribution of the prepolymer composition.

The polyimides prepared using the present invention also have high glass transition temperatures ($T_g$) exceeding 800° F., often surpassing 840° F. The thermooxidative stability of these polyimides is superior, the composites typically exhibiting weight losses of about 0.67 to about 4.7 weight percent after 100 hours of exposure at temperatures of about 700° F.

The facile processability and superior properties of the prepolymer composition and resultant polyimides make the prepolymer composition unique and readily adaptable for many industrial applications.

The following example describes a representative embodiment of the present invention.

EXAMPLE I (GLASS FIBER PREPREG)

A mixture of 32.34 g (0.11 mole) of 3,3′,4,4′-biphenyldianhydride was dissolved in a solvent comprising 38.4 g (1.2 mole) anhydrous methanol and 8 g (0.108 mole) ethyl acetate by heating at reflux for 19 hours. The concentration of ester in the solvent was about 70% by weight.

The ester solution was cooled to room temperature and added to a mixture of 7.78 g (0.072 mole) of meta-phenylenediamine and 5.18 g (0.048 mole) para-phenylenediamine dissolved in 30 mL of methanol.

A solution of nadic monomethyl ester in methanol was prepared by refluxing 1.64 g (0.01 mole) of nadic anhydride in 3 mL of methanol for an hour, and then cooled to room temperature.

The nadic monomethyl ester solution was added the phenylenediamine and ester solution to form a monomer solution, the resulting monomer solution was stirred overnight at room temperature to evaporate a portion of the solvent in the mixture, resulting in the formation of a slurry-like solid, having an ester:phenylenediamine:end cap molar ratio of 11:12:1. The concentration of prepolymer in the prepolymer composition was about 50–60% by weight.

The solidified prepolymer was applied to "S-2" type glass fiber fabric, manufactured by Corning Glass Company, Corning, N.Y., and heated to 100° C., until the solidified prepolymers melted and impregnated the glass fabric.

The impregnated fabric was then imidized by heating to 200° C. for 30 minutes, whereupon, the monomers in the fiber reacted to form single end capped, amine terminated, intermediate polyimide prepolymers, and the volatile byproducts of the reaction and residual methanol evaporated. An infrared absorption spectrum of this intermediate polyimide is virtually indistinguishable from that of the intermediate polyimide prepared by a procedure described in aforementioned patent application Ser. No. 07/816,304.

The prepreg was cured in a hydraulic press. The prepreg was placed in the press previously preheated to 500° F. The temperature of the press was gradually increased to 700° F. over a period of 45 minutes. When the mold temperature reached 475° F., a pressure of 200 psi was applied and maintained throughout the remainder of the molding cycle. The pressure dropped continuously to a temperature of about 530° F. due to melting and flow of the resin. When the mold temperature reached 700° F. it was held at this temperature for four hours, and then cooled to room temperature to form a uniform and substantially void-free fiber-reinforced composite article. The thermophysical and mechanical properties of the product are similar to those of polyimides processed according to the procedures described in aforementioned patent application Ser. No. 07/816,304.

Although the present invention has been discussed in considerable detail with reference to certain preferred versions thereof, other versions are possible. Therefore, the spirit and scope of the appended claims should not be limited to the description of the preferred versions contained herein.

What is claimed is:

1. A method of uniformly coating fibers with a substantially homogeneous, concentrated, prepolymer composition, the method comprising the steps of:
   (a) forming a homogeneous, concentrated, prepolymer composition by the steps of:
      i) forming an ester solution comprising dialkyl, trialkyl, or tetraalkylester of biphenyltetracarboxylic acid in a solvent comprising ethyl acetate and methanol, the molar ratio of the ethyl acetate to methanol being from about 1:3 to about 1:60;
      ii) adding diamine and end cap compound to the ester solution to form a monomer solution, the end cap compound characterized by (i) comprising a divalent compound, (ii) having at least one unsaturated moiety, (iii) reacts with the diamine or the ester to form an end cap radical that precludes further reaction of the diamine with the ester, and (iv) undergoes addition polymerization; and
      iii) evaporating a portion of the solvent from the monomer solution to form a substantially homogeneous, concentrated, prepolymer composition; and
   (b) coating fibers with the concentrated prepolymer composition by heating the prepolymer composition to an elevated temperature to form a prepolymer melt and applying the prepolymer melt to the fibers to substantially uniformly coat the fibers.

2. The method of claim 1, wherein the ethyl acetate to methanol molar ratio in step (a)(i) is from about 1:3 to about 1:20.

3. The method of claim 1, wherein the step of evaporating the solvent comprises evaporating the solvent until the concentration of prepolymers in the prepolymer composition is at least about 50% by weight.

4. An article of manufacture comprising fibers and polyimide, the article formed by the step of heating the coated fibers formed by the method of claim 1 to a temperature sufficiently high to cross-linking the prepolymer composition.

5. The article of manufacture of claim 4, wherein the article comprises polyimide having a $T_g$ of greater than about 800° F.

* * * * *